United States Patent
Pieroni

(10) Patent No.: US 8,147,122 B2
(45) Date of Patent: Apr. 3, 2012

(54) DISPENSING AND MIXING TIP FOR REACTIVE COMPONETS

(75) Inventor: Robert J. Pieroni, Lewes, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 10/793,579

(22) Filed: Mar. 4, 2004

(65) Prior Publication Data

US 2004/0257909 A1 Dec. 23, 2004

(51) Int. Cl.
  *B01F 7/00* (2006.01)
(52) U.S. Cl. .................. 366/171.1; 366/172.1; 366/307; 366/325.92; 366/329.1; 222/145.6
(58) Field of Classification Search ............... 222/145.5, 222/145.6; 366/172.1, 172.2, 176.1, 181.5, 366/307, 329.1, 339, 171.1, 302, 305, 325.92–325.93
See application file for complete search history.

(56) References Cited

U.S. PATENT DOCUMENTS

| | | | |
|---|---|---|---|
| 2,538,858 A | 1/1951 | Bodwell | |
| 3,241,722 A * | 3/1966 | Nissen | 222/136 |
| 3,767,085 A * | 10/1973 | Cannon et al. | 222/82 |
| 4,674,661 A | 6/1987 | Herold | |
| 4,846,373 A * | 7/1989 | Penn et al. | 222/137 |
| 4,967,933 A | 11/1990 | Maiorca et al. | |
| 4,986,443 A * | 1/1991 | Saur et al. | 222/1 |
| 4,988,015 A | 1/1991 | Price | |
| 5,020,694 A | 6/1991 | Pettengill | |
| 5,038,963 A | 8/1991 | Pettengill et al. | |
| 5,080,262 A * | 1/1992 | Herold et al. | 222/135 |
| 5,176,291 A | 1/1993 | Fillmore et al. | |
| 5,249,862 A | 10/1993 | Herold et al. | |
| 5,271,530 A | 12/1993 | Uehira et al. | |
| 5,286,105 A | 2/1994 | Herold et al. | |
| 5,289,949 A | 3/1994 | Gentile | |
| 5,320,250 A | 6/1994 | La et al. | |
| 5,332,122 A | 7/1994 | Herold et al. | |
| 5,332,124 A | 7/1994 | Cancro et al. | |
| 5,405,050 A | 4/1995 | Walsh | |
| 5,419,460 A | 5/1995 | Herold et al. | |
| 5,443,183 A * | 8/1995 | Jacobsen et al. | 222/145.6 |
| 5,501,368 A | 3/1996 | Brandhorst et al. | |
| 5,553,740 A | 9/1996 | King et al. | |
| 5,620,113 A | 4/1997 | Meshberg | |
| 5,647,510 A | 7/1997 | Keller | |
| 5,653,360 A | 8/1997 | Brandhorst et al. | |
| 5,699,934 A | 12/1997 | Kolcun et al. | |

(Continued)

FOREIGN PATENT DOCUMENTS

DE 3307558 A1 * 9/1984

(Continued)

*Primary Examiner* — Charles E Cooley
(74) *Attorney, Agent, or Firm* — Douglas J. Hura; Leana Levin; David Zdurne

(57) ABSTRACT

A tip (10) for mixing a plurality of components and for dispensing the mixture. The tip is particularly suited for use with a bulk supply of the components (11). The tip is further particularly suited for the mixing and dispensing of reactive materials. The tip (10) includes a housing (32) having a stator (31) positioned therein. The housing (32) includes a plurality of feeder channels (20, 21) that correspond to outlet channels of the bulk storage device. At least one of the feeder channels (20, 21) has a length dimension such that it extends into the outlet channel of the bulk storage device to prevent cross-contamination of the components held within the bulk storage device.

3 Claims, 7 Drawing Sheets

U.S. PATENT DOCUMENTS

| | | | |
|---|---|---|---|
| 5,823,389 A | 10/1998 | Guzowski | |
| 5,857,589 A | 1/1999 | Cline et al. | |
| 5,873,492 A | 2/1999 | Sullivan | |
| 5,928,213 A | 7/1999 | Barney et al. | |
| 5,941,416 A | 8/1999 | Balz et al. | |
| 5,992,686 A | 11/1999 | Cline et al. | |
| 6,012,610 A | 1/2000 | Pauser et al. | |
| 6,056,155 A | 5/2000 | Byerly et al. | |
| 6,089,407 A | 7/2000 | Gardos | |
| 6,129,244 A * | 10/2000 | Horth | 222/94 |
| 6,131,766 A | 10/2000 | King et al. | |
| 6,135,631 A * | 10/2000 | Keller | 366/339 |
| 6,206,244 B1 | 3/2001 | Muhlbauer | |
| 6,213,633 B1 * | 4/2001 | Kramer et al. | 366/339 |
| 6,244,740 B1 * | 6/2001 | Wagner et al. | 366/181.5 |
| 6,299,023 B1 | 10/2001 | Arnone | |
| 6,394,643 B1 * | 5/2002 | Bublewitz et al. | 366/172.1 |
| 6,443,612 B1 * | 9/2002 | Keller | 366/307 |
| 6,523,992 B1 * | 2/2003 | Bublewitz et al. | 366/172.1 |
| 6,540,395 B2 * | 4/2003 | Muhlbauer et al. | 366/307 |
| 6,612,465 B2 * | 9/2003 | Pierson et al. | 222/82 |
| 6,837,399 B1 * | 1/2005 | Wagner et al. | 222/145.6 |
| 6,837,612 B2 * | 1/2005 | Bublewitz et al. | 366/172.1 |
| 6,932,243 B2 * | 8/2005 | Keller | 222/145.6 |
| 7,287,898 B2 * | 10/2007 | Pauser et al. | 366/172.1 |
| 7,316,330 B2 * | 1/2008 | Muller et al. | 222/145.6 |
| 7,387,432 B2 * | 6/2008 | Lu et al. | 366/339 |
| 7,674,033 B2 * | 3/2010 | Pauser et al. | 366/172.1 |
| 2001/0005338 A1 * | 6/2001 | Muhlbauer et al. | 366/307 |
| 2003/0022128 A1 | 1/2003 | Heymann et al. | |
| 2003/0137898 A1 * | 7/2003 | Wagner et al. | 366/172.1 |
| 2004/0085854 A1 * | 5/2004 | Pauser et al. | 366/172.1 |
| 2004/0257909 A1 * | 12/2004 | Pieroni | 366/172.1 |
| 2005/0232073 A1 * | 10/2005 | Wagner et al. | 366/172.1 |
| 2007/0175921 A1 * | 8/2007 | Keller | 222/137 |
| 2008/0251535 A1 * | 10/2008 | Suchan et al. | 222/83 |
| 2010/0200614 A1 * | 8/2010 | Von Rotz et al. | 222/145.5 |
| 2010/0252574 A1 * | 10/2010 | Busin | 222/137 |

FOREIGN PATENT DOCUMENTS

| | | |
|---|---|---|
| DE | 4235736 C1 * | 3/1994 |
| EP | 0 151 922 | 8/1985 |
| EP | 0313519 A1 * | 4/1989 |
| EP | 0 541 972 | 5/1993 |
| EP | 1149627 A2 * | 10/2005 |
| JP | 03143537 A * | 6/1991 |
| WO | 98/43727 * | 10/1998 |
| WO | WO 00/21652 | 4/2000 |
| WO | WO 2004080611 A1 * | 9/2004 |
| WO | 01/24919 * | 4/2005 |
| WO | WO 2006039827 A1 * | 4/2006 |

* cited by examiner

DISPENSING AND MIXING TIP FOR REACTIVE COMPONETS

TECHNICAL FIELD

The present invention is a tip for mixing a plurality of components and for dispensing the mixture. The tip is particularly suited for use with a bulk supply of the components. The tip is further particularly suited for the mixing and dispensing of reactive materials.

BACKGROUND OF THE INVENTION

Tips that both mix and dispense materials are known in the art. For example, U.S. Pat. No. 5,249,862 discloses such a tip which is particularly suited for the mixing and dispensing of dental impression materials. In may circumstances, a plurality of pre-mix components are housed separately, such as in separate areas of a single bulk storage device. When a quantity of the mixture of the components is needed, the separate components are caused to flow into the mix tip where they are mixed and then dispensed therefrom. This may be the case for example, when a base and a catalyst are employed in a dental impression material. This type of mix tip is often associated for use with a powered bulk storage device that imparts torque to a stator within the mix tip, causing the stator to rotate to effect mixing and advancing of the mixed components through the tip to be dispensed.

As noted in the '862 patent, cross-contamination between the components should be avoided as much as possible until desired. Any cross-contamination between the components in the bulk storage device itself could block the output of the device or prematurely react the components. Neither situation is normally desirable.

A need exists therefore, for a mixing and dispensing tip for a plurality of materials, particularly a tip designed to be employed with a bulk storage device. Such a tip should help prevent unwanted cross-contamination within the bulk storage device or its outlet channels. The tip should be improved with respect to its ability to intimately mix the components.

DISCLOSURE OF THE INVENTION

A tip for mixing and dispensing a plurality of components has extended feeder channels that individually correspond to complementary outlet channels in a bulk storage device. The number of feeder channels in the tip should be at least as many separate outlet channels in the bulk storage device, which often will correspond to the number of individual components stored in the bulk storage device. For the sake of this discussion, the invention will herein be described as having two such feeder channels. Because the feeder channels in the mix tip are extended beyond those heretofore known in the art, thereby effectively preventing cross-contamination, the mix tip can be used as a cap for the bulk storage device until removed for a subsequent procedure.

The feeder channels are configured to have a cross-section suitable for components to be mixed, such that a predetermined amount of each component is caused to pass into the mixing area of the tip, based upon that cross-section. The amount of each component required may be different, and hence, the cross-sections of the feeder channels may be different or if needed, the same. The length of the channels can also be configured such that prior to use, the level of components within the outlet channels of the bulk storage device are relatively equal due to the previous use. This leads to less waste of the components in subsequent procedures.

The mix tip has a stator element and a housing. The mixing tip stator does not contact or scrape the back wall of the tip housing. The gap helps prevent product flow and is directed by curved paddles. As the product flows around the mixing element or stator, it sweeps into neck of the housing. The housing has a plurality and preferably four internally molded helix lands and grooves which mix and help push the mixed product out of the tip. The stator has mix elements which are preferably longitudinally disposed on the stator, such that as the stator rotates, the mix elements cause the components to physically contact the lands and grooves. This causes the components to be mixed and to traverse longitudinally through the mix tip toward a discharge opening therein.

PREFERRED EMBODIMENTS FOR CARRYING OUT THE INVENTION

A mix tip 10 is preferably configured to be employed with a bulk storage device 11. For exemplary purposes, bulk storage device 11 is shown as having two separate component compartments 12 and 13. It is preferred that bulk storage device 11 be employed with a conventional powered dispensing device (not shown) at the point of use. The bulk storage device 11 is placed into the powered dispensing device, and a force is caused to push or otherwise cause flow of material within bulk storage device compartments 12 and 13 toward a discharge end, at which mix tip 10 is proximately positioned.

Figure 7:
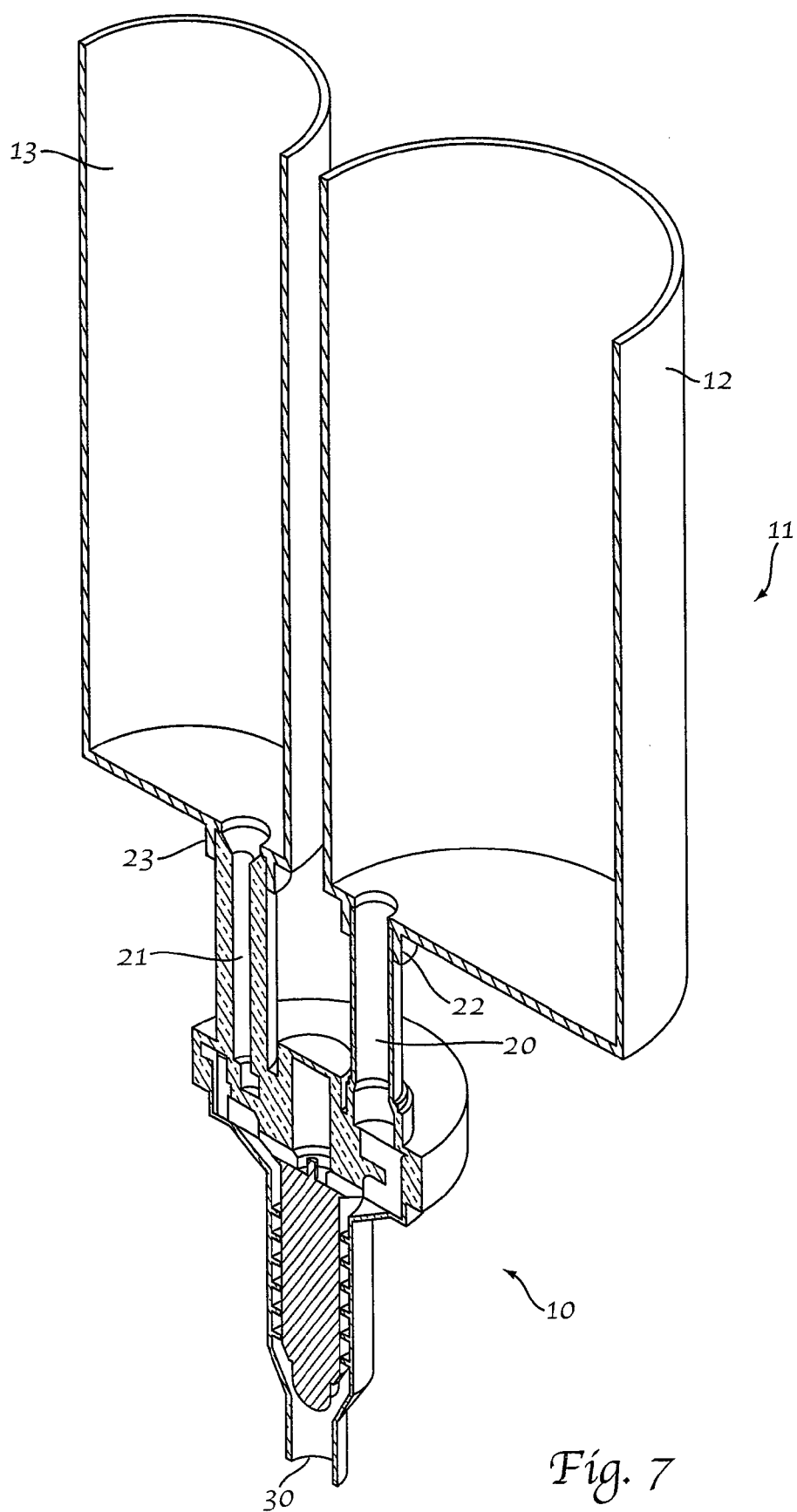
FIG. 7 is a side elevational, sectional view of the mix tip and bulk storage device of FIG. 1.

Mix tip 10 is therefore, useful for mixing and dispensing a plurality of components such as may be initially held in compartments 12 and 13. Mix tip 10 preferably has extended feeder channels 20 and 21 that individually correspond to complementary outlet channels 22 and 23 in a bulk storage device (FIG. 7). The number of feeder channels in the tip should be at least as many separate outlet channels in the bulk storage device, which often will correspond to the number of individual components stored in the bulk storage device. For the sake of this discussion, the invention will herein be described as having two such feeder channels. By "complementary" it is intended to mean that the two can physically cooperate, such as by a press fit or the like, to form a continuous pathway from the bulk storage device 11 to the mix tip 10 and ultimately to the discharge orifice 30 of mix tip 10. In one embodiment, the outlet channels 22 and 23 in bulk storage device 11 form sockets which physically receive extended feeder channels 20 and 21 respectively to form such a continuous pathway.

Because the feeder channels in the mix tip are extended beyond those heretofore known in the art, thereby effectively preventing cross-contamination, the mix tip can be used as a cap for the bulk storage device until removed for a subsequent procedure. Mix tips previously known in the art were provided with relatively short feeder channels. According to the present invention, the feeder channels 21 and 20 of mix tip 10 are extended, such that they are approximately about one-quarter to three quarters, more preferably about one-half the length of the mix tip 10. Of course they can be more or less and still be within the scope of the invention, as long as they are long enough to effectively present cross contamination which was known with shorter feeder channels.

Figure 1:
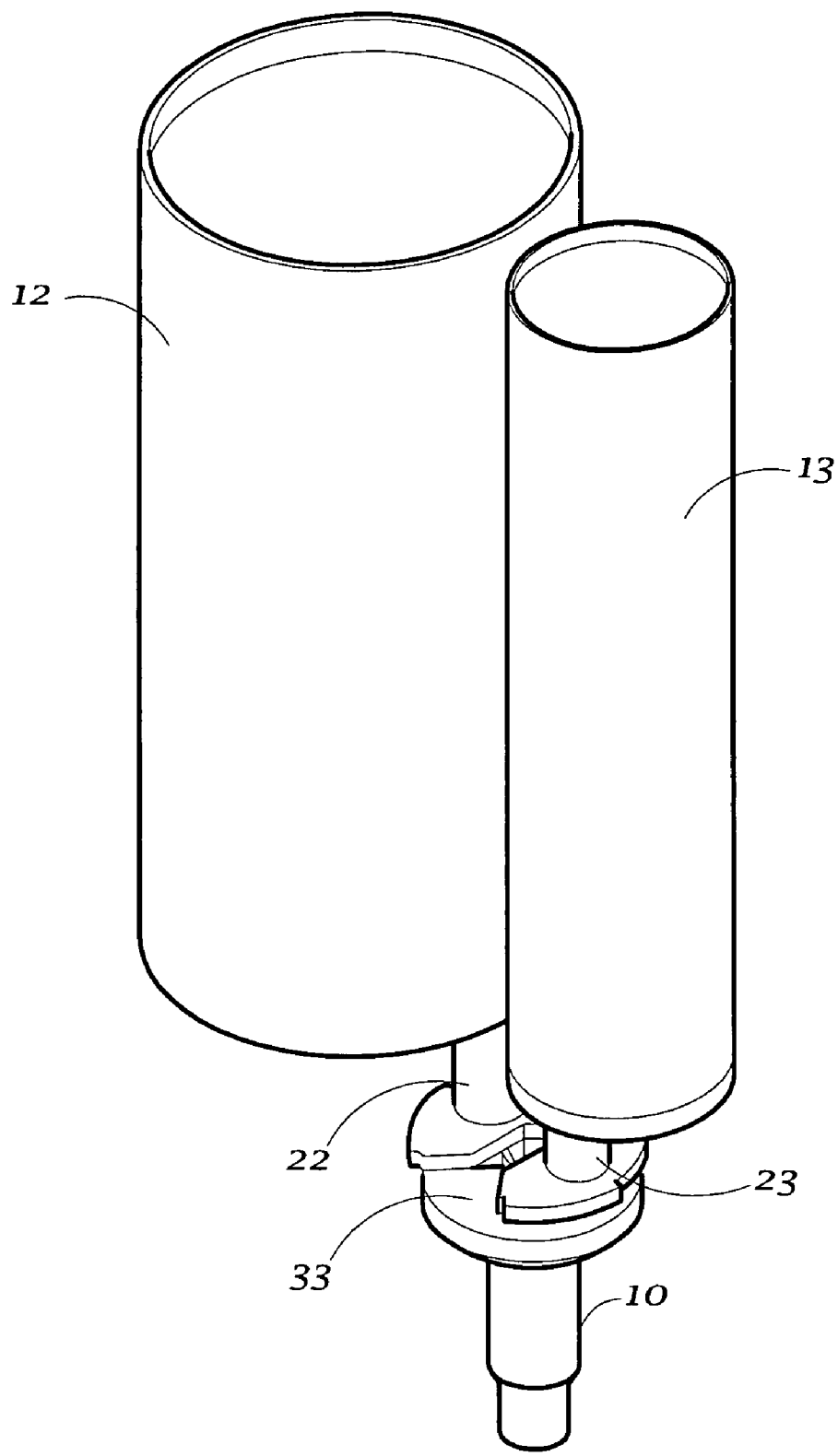
FIG. 1 is a perspective view of a mix tip according to the present invention, and shown for environmental purposes affixed to a bulk storage device.
Figure 2:
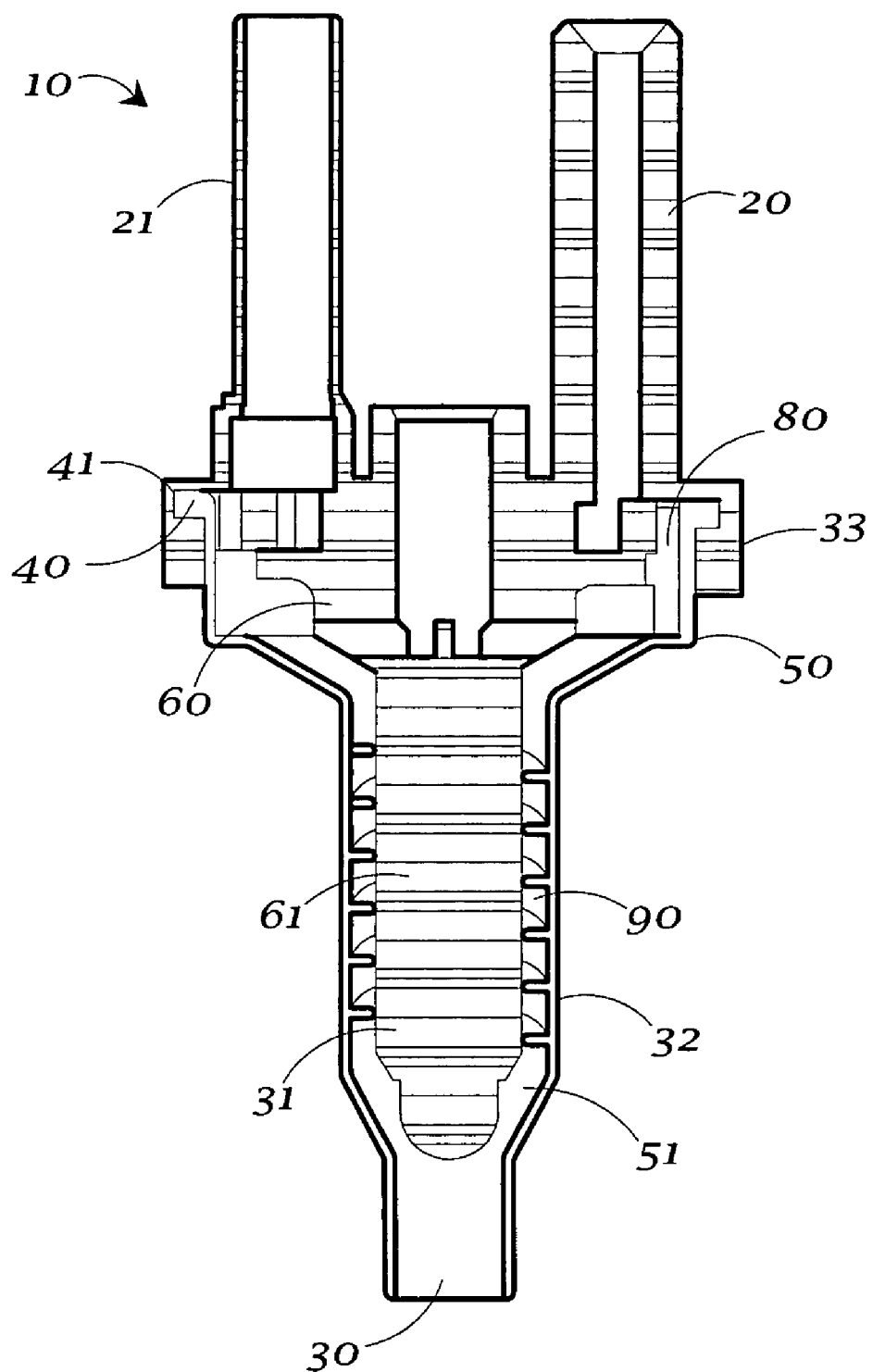
FIG. 2 is a side, sectional view of the mix tip of FIG. 1.
Figure 3:
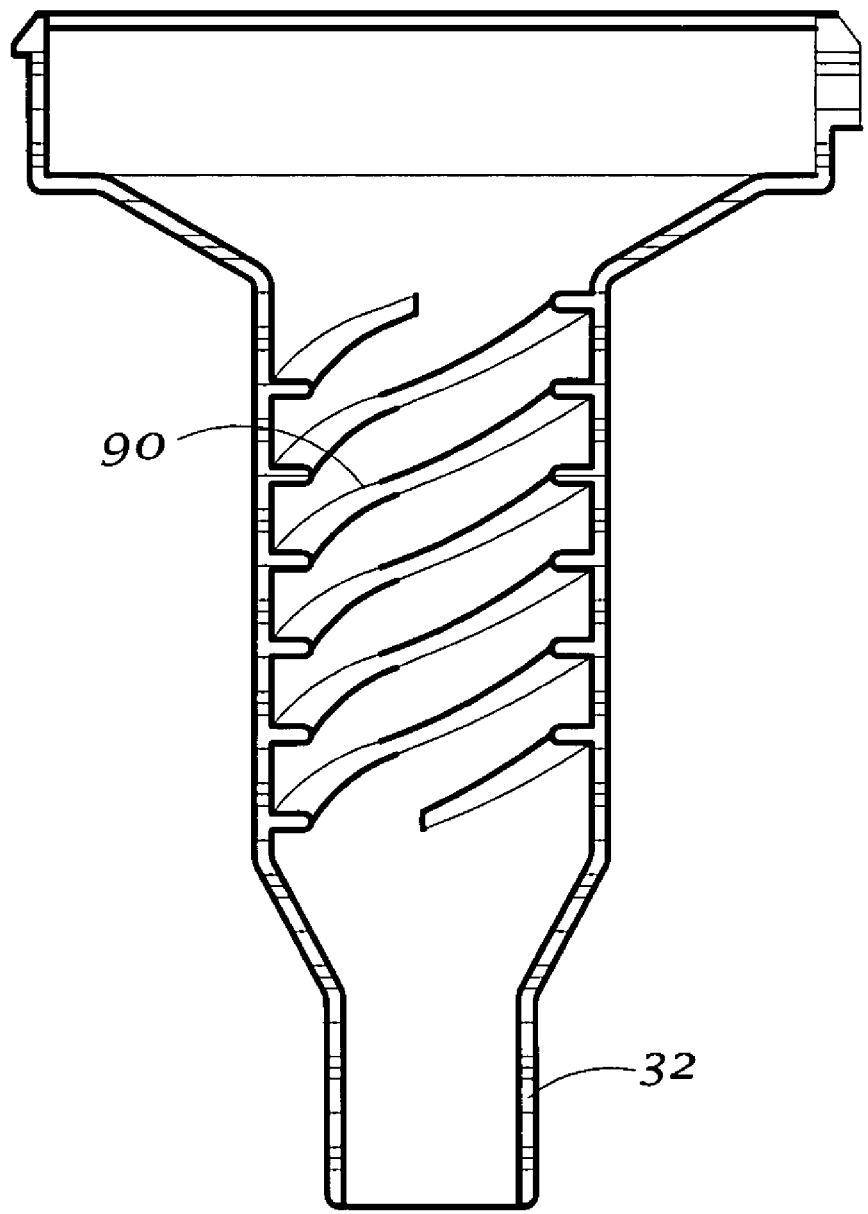
FIG. 3 is a side, sectional view of one portion of the mix tip of FIG. 2, namely, the housing thereof.

The feeder channels 20 and 21 are configured to have a cross-section suitable for components to be mixed, such that a predetermined amount of each component is caused to pass into the mixing area of the tip, based upon that cross-section (FIG. 2). The amount of each component required may be different, and hence, the cross-sections of the feeder channels may be different or if needed, the same. The length of the channels can also be configured such that prior to use, the level of components within the outlet channels of the bulk storage device are relatively equal due to the previous use. This leads to less waste of the components in subsequent procedures.

The mix tip has a stator element 31, and upper housing 32 and a lower housing 33. The lower housing 33 carries and is preferably integrally formed with feeder channels 20 and 21. Upper housing 32 is configured to be affixable, either permanently or temporarily, to lower housing 33, trapping stator element 31 therein in a manner that allows stator element 31 freedom to rotate therein. This affixing may be accomplished by any means including adhesive bonding, welding or the like, or a physical interaction with a latch mechanism, such as by the physical contact and cooperation between a lip 40 and detent 41. Upper housing 32 is preferably provided with a base portion 50 opening into a stator receiving portion 51. Stator 31 is similarly provided with a stator base portion 60 and an elongate portion 61, such that in use, elongate portion 61 is received within stator receiving portion 51. Stator 31 elongate portion 61 is provided with protrusions 70 that are preferably longitudinally projected from elongate portion 61. Protrusions 70 physically interact and cooperate with upper housing 32 in a manner to be below described.

Figure 5:
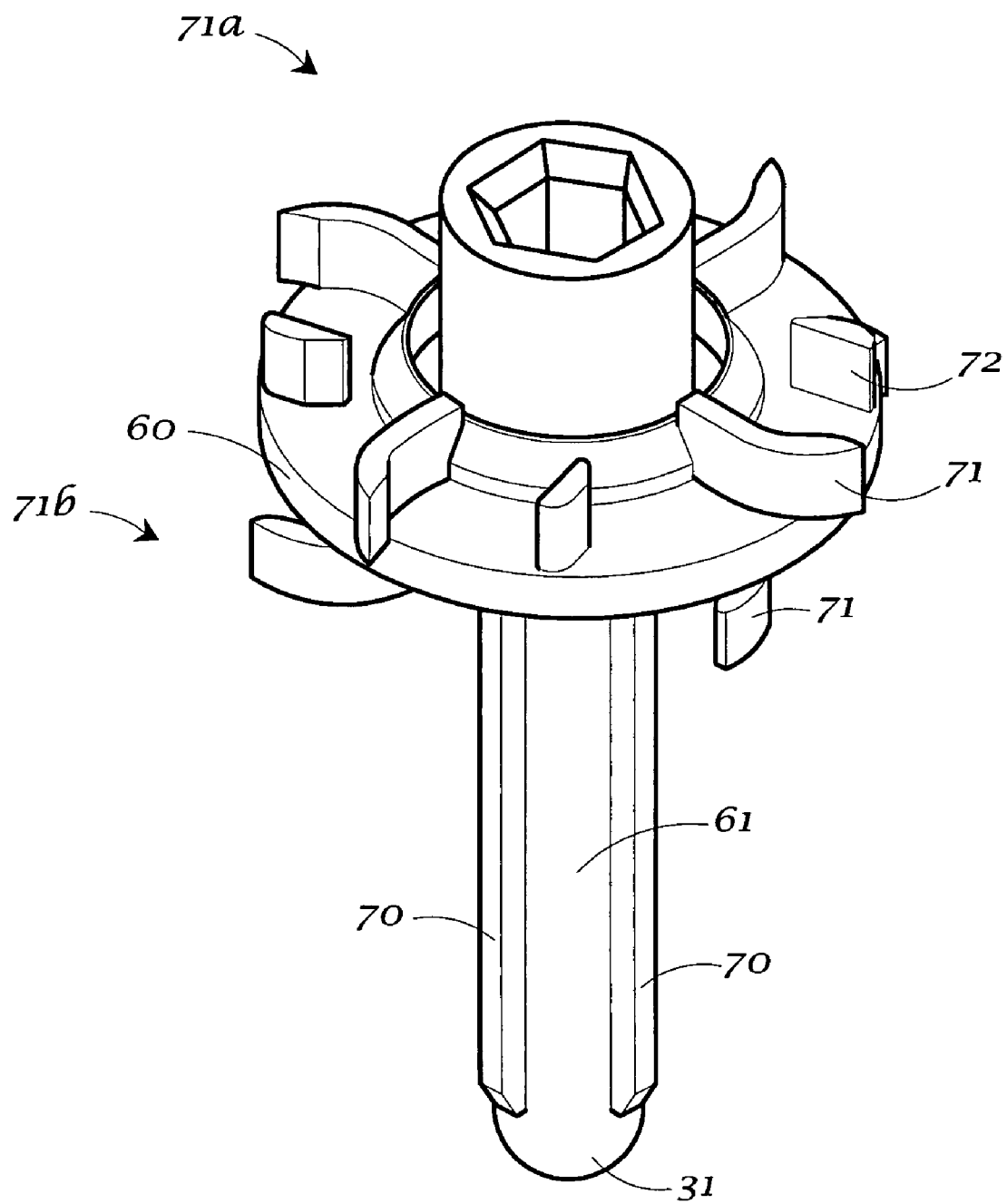
FIG. 5 is a perspective view of a stator element portion of the tip of FIG. 2.
Figure 6:
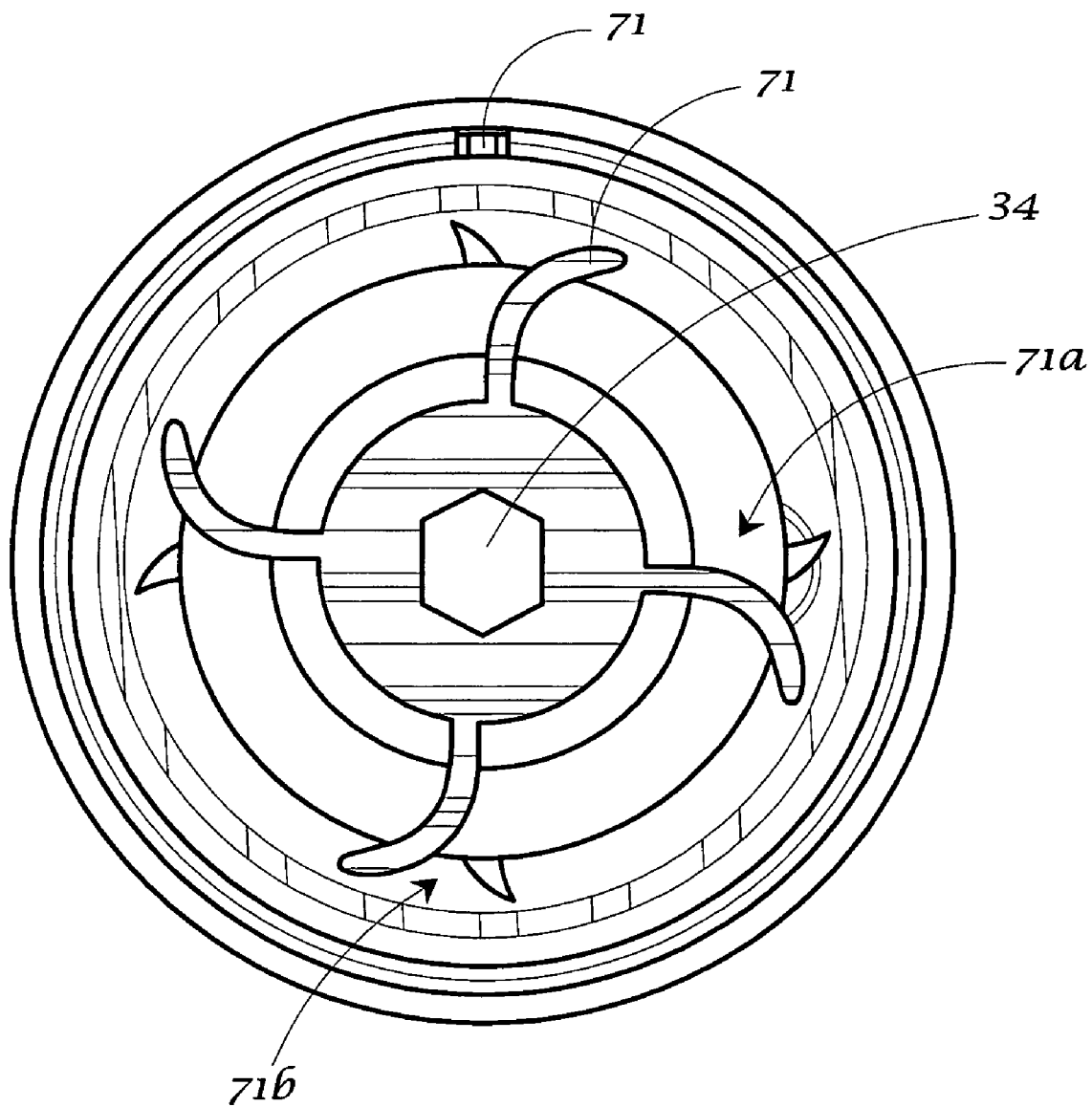
FIG. 6 is a bottom, plan view of the stator element of FIG. 5.

Stator element 31 base portion 60 is preferably provided with a plurality of sweeping mix elements 71. More preferably, stator base portion 60 is provided with a first and a second set of sweeping mix elements 71. Sweeping mix elements 71 are preferably curved. As shown in FIG. 5, a first set of curved sweeping elements 71a is positioned in a spaced opposing relationship to a second set of curved sweeping mix elements 71b. This allows sweep mixing no matter in which direction stator element 31 is rotated. Some means is provided to affix stator element 31 to a power drive (not shown) of a dispensing device to impart the above described torque power to rotate stator element 31 within upper housing 32. For example, a collet 34 may be affixed to or integrally formed with stator element 31 to physically interact (not shown) with such a powered device. Further, stator element 31 may also be provided with any number or shape of intermediate sweep paddles or mix elements, such as paddles 72.

Stator element 31 preferably does not contact or scrape the lower housing 33 when in place. A gap 80 formed therebetween helps prevent product flow that is directed by sweeping mix elements 71. As the product flows around the stator element 31, it is swept into stator receiving portion 51 of upper housing 32.

Figure 4:
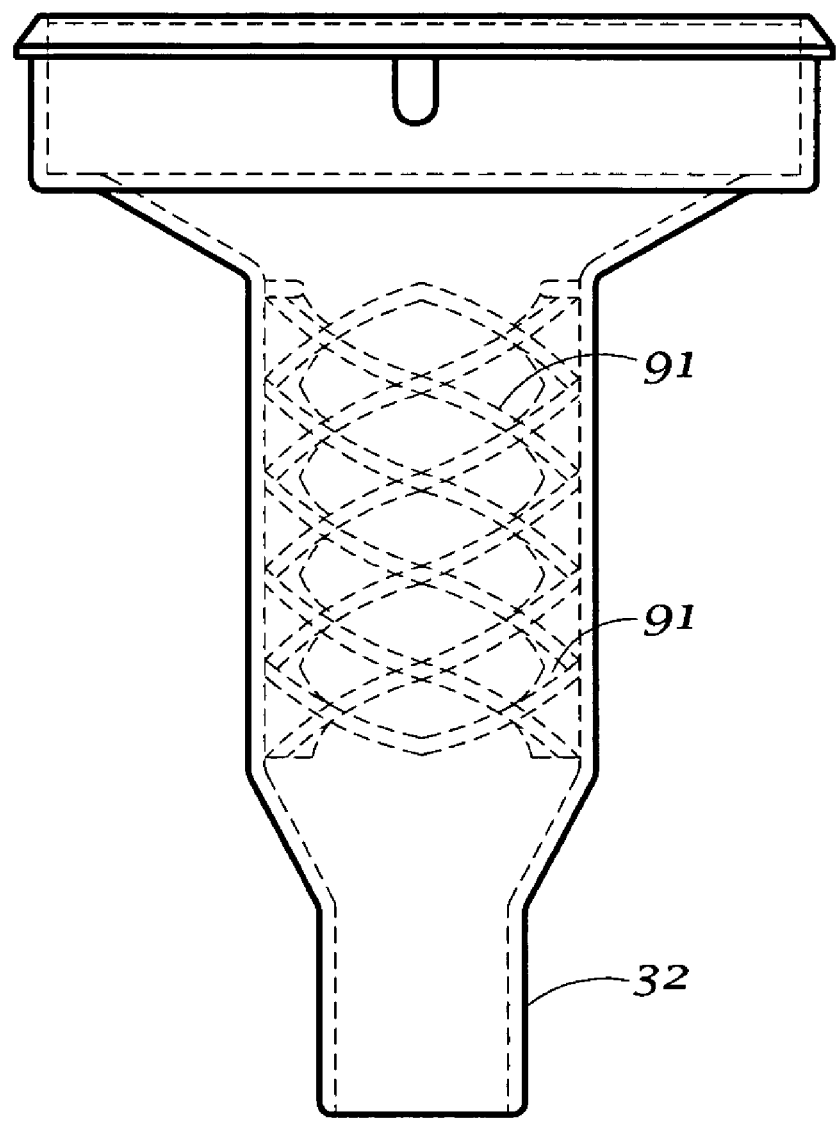
FIG. 4 is an alternative embodiment of the housing of FIG. 3.

Upper housing 32 is preferably hollow such that it has an interior surface. The interior surface of upper housing 32 has a plurality and preferably four internally molded helix threads 90, which mix and help push the mixed product out of the mixing tip 10. The stator element protrusions 70 are affixed to or more preferably integrally formed with stator element 31, such that as the stator element 31 rotates, the protrusions 70 cause the components to physically contact threads 90. This causes the components to be mixed and to traverse longitudinally through the mix tip 10 toward discharge orifice 30 therein. Upper housing 32 threads 90 may be of any configuration, including a single helix, a double helix or a greater plurality of such helix threads. A double helix thread 91 is shown in FIG. 4.

What is claimed is:

1. A tip for mixing and dispensing a plurality of components from a bulk storage device of the type having a plurality of outlet channels, comprising:

a housing having a length dimension and a stator element positioned within said housing, said housing having means to releasably attach to the bulk storage device and a plurality of feeder channels that fluidly connect with the outlet channels when said tip is attached to the bulk storage device, said plurality of feeder channels being juxtaposed to said housing; at least one of said feeder channels having a length dimension that is about one-quarter to about three quarters said length dimension of said housing, wherein the stator element includes a stator base portion having a plurality of sweeping mix elements having a curved configuration and a stator elongate portion having protrusions that are longitudinally projected from the stator elongate portion, wherein the housing has at least one mixing helical thread that interacts with the protrusions of the stator elongate portion such that the plurality of components are mixed and traverse the length dimension of the housing toward a discharge orifice.

2. A mix tip as in claim 1, wherein said feeder channels are configured to have a predetermined cross-section such that a predetermined amount of each component is caused to flow therethrough.

3. A mix tip as in claim 2, wherein the cross-section of at least two of said plurality of feeder channels are different.

* * * * *